(12) United States Patent
Seyfang et al.

(10) Patent No.: US 9,492,455 B1
(45) Date of Patent: Nov. 15, 2016

(54) METHODS OF TREATING NFA-1 ORGANISM INFECTION USING APOCYNIN

(71) Applicants: Andreas Seyfang, Tampa, FL (US); Adarsh Bellur, Gainesville, FL (US); DeAndre Wells, Punta Gorda, FL (US); Matthew Doenges, Boynton Beach, FL (US)

(72) Inventors: Andreas Seyfang, Tampa, FL (US); Adarsh Bellur, Gainesville, FL (US); DeAndre Wells, Punta Gorda, FL (US); Matthew Doenges, Boynton Beach, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/623,887

(22) Filed: Feb. 17, 2015

Related U.S. Application Data

(60) Provisional application No. 61/940,683, filed on Feb. 17, 2014.

(51) Int. Cl.
| | | |
|---|---|---|
| *C07C 39/08* | (2006.01) |
| *A61K 31/52* | (2006.01) |
| *A61K 31/519* | (2006.01) |
| *A61K 31/11* | (2006.01) |
| *A61K 31/085* | (2006.01) |

(52) U.S. Cl.
CPC ............. *A61K 31/52* (2013.01); *A61K 31/085* (2013.01); *A61K 31/11* (2013.01); *A61K 31/519* (2013.01)

(58) Field of Classification Search
CPC .................................................... C07C 39/08
USPC ........................................................ 568/716
See application file for complete search history.

(56) References Cited

U.S. PATENT DOCUMENTS

2009/0110673 A1* 4/2009 Vanden Hoek ........ A61K 31/00
424/94.1

FOREIGN PATENT DOCUMENTS

WO       0076316 A1    12/2000

OTHER PUBLICATIONS

Chapdelaine, et al., "Preliminary Report on Drug Research Involving Acanthamoeba and Naegleria", The Arthritis Trust of America, 1984, p. 1-3.
Song, et al., "Reactive Oxygen Species-Dependent Necroptosis in Jurkat T Cells Induced by Pathogenic Free-Living Naegleria Fowleri", Parasite Immunology, 2011, 33, 390-400.
Kim, et al., "NOX1 Participates in ROS-Dependent Cell Death of Colon Epithelial Caco2 Cells Induced by Entamoeba Histolytica", Microbes and Infection 13 (2011) 1052-1061.
Jeong, et al., "Expression of the nfa1 Gene Cloned from Pathogenic Naegleria Fowleri in Nonpathogenic N. Gruberi Enhances Cytotoxicity Against CHO Target Cells in Vitro", Infection and Immunity, Jul. 2005, p. 4098-4105, vol. 73, No. 7.
Kang, et al., "Role of the Nfa1 Protein in Pathogenic Naegleria Fowleri Cocultured with CHO Target Cells", Clinical and Diagnostic Laboratory Immunology, Jul. 2005, p. 873-876, vol. 12, No. 7.
Visvesvara, et al., "Pathogenic and Opporunistic Free-Living Amoebae: *Acanthamoeba* spp., *Balamuthia mandrillaris, Negleria fowleri, and Sappinia diploidea*", Federation of EP Microbiological Societies, 2007.

* cited by examiner

*Primary Examiner* — Douglas M Willis
(74) *Attorney, Agent, or Firm* — Thomas | Horstemeyer, LLP

(57) ABSTRACT

Described herein are compounds and pharmaceutical formulations thereof that can be administered to a subject infected with or suspected of being infected with an organism having an Nfa-1 protein. Also provided herein are methods of treating an infection with an organism having an Nfa-1 protein in a subject in need thereof by administering a therapeutically effective amount of apocynin to the subject in need thereof.

4 Claims, 12 Drawing Sheets

```
N.fowleri Nfa1   11  WDSSFCVGNNELNEQKKLFALINALDA----------NRSSASALKELLDFVVMKKA   60
                     W  S  VG  +  ++ ++L   IN L A          +   S L+ L+D+
Acanthamoeba    537  WTDSLSVGVKKFDKAQRLVEYINVLFAIIGTQEKDKRKQQITSLLQCLIDYTQYAQ   596

N.fowleri Nfa1   61  EDLFAKVNFSDSTSKETDKFVQDALGLKTVGDAEI-QFIKQWLVNIKGSMKYKGVL*  119
                     E+LF ++N+ D   E  K  Q         K++   +++  +F+++WL++ I   MKYK
Acanthamoeba    597  EELFTQLNYPDEAGVEQFCKLQKG---KSINLSKLAKFLREWLLIMEDMKYKPFFHQHNIY*  659
```

Fig. 5

**Initial-Rate Oxidoreductase Enzyme Kinetics of *N. fowleri* Nfa-1 Hemerythrin using NADH and NADPH as Substrates.**

| *N. fowleri* Nfa-1 Substrate | $k_{cat}$ ($sec^{-1}$) | $K_m$ (μM) | $k_{cat}/K_m$ ($sec^{-1}$ $M^{-1}$) | $V_{max}$ (μmol/min/mg protein) |
|---|---|---|---|---|
| NADH | 4.4 ± 0.3 | 64.5 ± 9.8 | 0.68 x $10^5$ | 19.7 ± 1.1 |
| NADPH | 3.3 ± 0.1 | 22.3 ± 2.9 | 1.48 x $10^5$ | 14.7 ± 0.6 |

SEQ ID NO: 3

$M_1$ATTIPSPFNWDSSFCVGNNELNEQHKKLFALINALDANRSSASALKELL
DFVVMHFKAEEDLFAKVNFSDSTSHKETHDKFVQDALGLKTVGDAEIQFI
KQWLVNHIKGSDMKYKGVL$_{119}$

Fig. 12A

SEQ ID NO: 4

$A_1$TGGCCACTACTATTCCATCACCATTCAACTGGGACTCTTCTTTCTGC
GTTGGTAACAATGAATTGAATGAGCAACACAAGAAGCTCTTTGCTCTC
ATCAATGCTTTGGATGCCAACAGATCCAGTGCTTCAGCATTGAAGGAA
TTGCTTGATTTCGTCGTTATGCATTTCAAGGCTGAGGAGGACTTGTTC
GCAAAGGTGAATTTCTCTGATTCTACTTCTCACAAAGAGACTCATGATA
AGTTTGTTCAAGATGCTTTGGGTTTGAAGACTGTTGGAGATGCTGAAA
TTCAATTCATCAAGCAATGGTTGGTGAATCACATTAAGGGATCTGATAT
GAAGTACAAGGGAGTGCTTTAA$_{360}$

Fig. 12B

```
                        SEQUENCE LISTING

<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: PCR forward primer for Nfa-1 from N. fowleri
      cloning with NdeI site.

<400> SEQUENCE: 1
tagctacata tggccactac tattccatca ccattc                              36

<210> SEQ ID NO 2
<211> LENGTH: 43
<212> TYPE: DNA
<213> ORGANISM: Artificial Sequence
<220> FEATURE:
<223> OTHER INFORMATION: Reverse primer for Nfa-1 from N. fowleri
      cloning with SapI site

<400> SEQUENCE: 2
cagtatgctc ttctgcaaag cactcccttg tacttcatat cag                      43

<210> SEQ ID NO 3
<211> LENGTH: 119
<212> TYPE: PRT
<213> ORGANISM: Naegleria fowleri

<400> SEQUENCE: 3

Met Ala Thr Thr Ile Pro Ser Pro Phe Asn Trp Asp Ser Ser Phe Cys
1               5                   10                  15

Val Gly Asn Asn Glu Leu Asn Glu Gln His Lys Lys Leu Phe Ala Leu
            20                  25                  30

Ile Asn Ala Leu Asp Ala Asn Arg Ser Ser Ala Ser Ala Leu Lys Glu
        35                  40                  45

Leu Leu Asp Phe Val Val Met His Phe Lys Ala Glu Glu Asp Leu Phe
    50                  55                  60
```

```
Ala Lys Val Asn Phe Ser Asp Ser Thr Ser His Lys Glu Thr His Asp
 65                  70                  75                  80

Lys Phe Val Gln Asp Ala Leu Gly Leu Lys Thr Val Gly Asp Ala Glu
                 85                  90                  95

Ile Gln Phe Ile Lys Gln Trp Leu Val Asn His Ile Lys Gly Ser Asp
            100                 105                 110

Met Lys Tyr Lys Gly Val Leu
        115

<210> SEQ ID NO 4
<211> LENGTH: 360
<212> TYPE: DNA
<213> ORGANISM: Naegleria fowleri

<400> SEQUENCE: 4
atggccacta ctattccatc accattcaac tgggactctt ctttctgcgt tggtaacaat      60
gaattgaatg agcaacacaa gaagctcttt gctctcatca atgctttgga tgccaacaga    120
tccagtgctt cagcattgaa ggaattgctt gatttcgtcg ttatgcattt caaggctgag    180
gaggacttgt tcgcaaaggt gaatttctct gattctactt ctcacaaaga gactcatgat    240
aagtttgttc aagatgcttt gggtttgaag actgttggag atgctgaaat tcaattcatc    300
aagcaatggt tggtgaatca cattaaggga tctgatatga agtacaaggg agtgctttaa    360
```

METHODS OF TREATING NFA-1 ORGANISM INFECTION USING APOCYNIN

CROSS-REFERENCE TO RELATED APPLICATIONS

This application claims the benefit of U.S. provisional patent application Ser. No. 61/940,683 filed on Feb. 17, 2014, having the title "Inhibitors Against NAD(P)H Oxidases and ROS Production Protect Against Cytotoxicity of Pathogenic Amoebae," the disclosure of which is incorporated herein in its entirety.

SEQUENCE LISTING

This application contains a sequence listing filed in electronic form as an ASCII.txt file entitled 02152701.txt, created on Feb. 13, 2015 and having a size of 2,376 bytes. The content of the sequence listing is incorporated herein in its entirety.

BACKGROUND

Free-living amoebae can be pathogenic and cause severe infection that can result in debilitation or death. For some infections the death rate exceeds 95%. The high death tolls can be attributed, at least in part, to the lack of effective treatments. As such there exists a need for the development of improved treatments for amoebae infections.

SUMMARY

Pharmaceutical formulations containing an amount of a compound that can inhibit an Nfa-1 protein are provided. In some aspects, the pharmaceutical formulations contain a therapeutically effective amount of a compound according to formula I or a derivative thereof Formula I 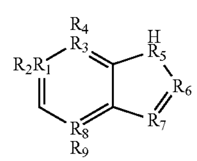 to reduce cytoxicity in a subject suspected of being infected or infected with an organism having an Nfa-1 protein, where $R_1$ can be N or C, $R_2$ is O can be H, $R_3$ is N can be C, $R_4$ can be H, OH, O, or S, $R_5$ can be N or C, $R_6$ can be N or C, $R_7$ can be N or C, $R_8$ can be N or C, and $R_9$ can be H or O. In some aspects, the compound of Formula I can be a compound according to Formula II, Formula III, Formula IV, or Formula V, or derivatives of compounds according to Formula II, Formula III, Formula IV, or Formula V. The organism having an Nfa-1 protein can be *N. fowleri, N. gruberi, Acanthamoeba hatchetti, A. healyi, A. polyphaga, A. rhysodes, A. astronyxis, A. divionensis, A castellanii, Entamoeba histolytica, E. invadens, E. dispar, Balamuthia mandrillaris, Sappinia diploidea, Pyrococcus furiosus, Clostridium acetobutylicum, Desulfovibrio vulgaris, Burkholderia pseudomallei, Desulfurococcus mucosus, Methanococcus jannaschii, Riftia pachyptila, Phascolopsis gouldii, Periserrula leucophryna, Perinereis aibuhitensis, Theromyzon tessulatum, Hirudo medicinalis*, or *Themiste zostericola*. The therapeutically effective amount of Formula I, Formula II, Formula III, Formula IV, Formula V or a derivative of any of the foregoing compounds can, in some aspects, can reduce the oxidoreductase activity of the Nfa-1 protein as compared to a control in the subject suspected of being infected or infected with the organism having the Nfa 1 protein. In additional aspects, the therapeutically effective amount of Formula I, Formula II, Formula III, Formula IV, Formula V or a derivative of any of the foregoing compounds can reduce the amount of reactive oxygen species in the subject suspected of being infected or infected with the organism having an Nfa-1 protein as compared to a control.

In further aspects, the pharmaceutical formulations contain a therapeutically effective amount of a compound to formula VI or a derivative thereof Formula VI 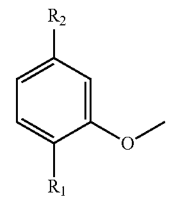 to reduce cytoxicity in a subject suspected of being infected or infected with an organism having an Nfa-1 protein, where $R_1$ can be H or OH, and $R_2$ can be H, $COCH_3$, or COH. In other aspects, the compound according to formula VI can be a compound according to Formula VII, Formula VIII, Formula IX, or Formula X, or derivatives of compounds according to Formula VII, Formula VIII, Formula IX, or Formula X. The organism having an Nfa-1 protein can be *N. fowleri, N. gruberi, Acanthamoeba hatchetti, A. healyi, A. polyphaga, A. rhysodes, A. astronyxis, A. divionensis, A. castellanii, Entamoeba histolytica, E. invadens, E. dispar, Balamuthia mandrillaris, Sappinia diploidea, Pyrococcus furiosus, Clostridium acetobutylicum, Desulfovibrio vulgaris, Burkholderia pseudomallei, Desulfurococcus mucosus, Methanococcus jannaschii, Riftia pachyptila, Phascolopsis gouldii, Periserrula leucophryna, Perinereis aibuhitensis, Theromyzon tessulatum, Hirudo medicinalis*, or *Themiste zostericola*. The therapeutically effective amount of Formulas VI, Formula VII, Formula VIII, Formula IX, or Formula X, or derivatives of any of the foregoing compounds can, in some aspects, can reduce the oxidoreductase activity of the Nfa-1 protein as compared to a control in the subject suspected of being infected or infected with the organism having the Nfa 1 protein. In additional aspects, the therapeutically effective amount of Formulas VI, Formula VII, Formula VIII, Formula IX, or Formula X, or derivatives of any of the foregoing compounds can reduce the amount of reactive oxygen species in the subject suspected of being infected or infected with the organism having an Nfa-1 protein as compared to a control.

Methods of using the pharmaceutical formulations containing an amount of a compound that can inhibit an Nfa-1 protein are provided. In some aspects, the method contains the step of administering a therapeutically effective amount of Formula I or a derivative thereof:

Formula I to a subject in need thereof, where the subject in need thereof is infected with or is suspected of being infected with at least one organism having an Nfa-1 protein, and where $R_1$ is N or C, $R_2$ is O or H, $R_3$ is N or C, $R_4$ is H, OH, O, or S, $R_5$ is N or C, $R_6$ is N or C, $R_7$ is N or C, $R_8$ is N or C, and $R_9$ is H or O. In further aspects, the therapeutically effective amount adminstered can reduce cytotoxicity in the subject in need thereof as compared to a control. The therapeutically effective amount, in other aspects, can the amount of reactive oxygen species in the subject in need thereof as compared to a control. In additional aspects, the therapeutically effective amount can reduce the oxidoreductase activity of the Nfa-1 protein as compared to a control. The organism having the Nfa-1 protein can be *N. fowleri*, *N. gruberi*, *Acanthamoeba hatchetti*, *A. healyi*, *A. polyphaga*, *A. rhysodes*, *A. astronyxis*, *A. divionensis*, *A. castellanii*, *Entamoeba histolytica*, *E. invadens*, *E. dispar*, *Balamuthia mandrillaris*, *Sappinia diploidea*, *Pyrococcus furiosus*, *Clostridium acetobutylicum*, *Desulfovibrio vulgaris*, *Burkholderia pseudomallei*, *Desulfurococcus mucosus*, *Methanococcus jannaschii*, *Riftia pachyptila*, *Phascolopsis gouldii*, *Periserrula leucophryna*, *Perinereis aibuhitensis*, *Theromyzon tessulatum*, *Hirudo medicinalis*, or *Themiste zostericola*. In some aspects of the method, the compound of Formula I can be a compound according to Formula II, Formula III, Formula IV, Formula V or a derivative of any of the foregoing compounds.

In other aspects, the method contains the step of administering a therapeutically effective amount of Formula IV or a derivative thereof:

Formula VI to a subject in need thereof, where the subject in need thereof is infected with or is suspected of being infected with at least one organism having an Nfa-1 protein, and $R_1$ can be H or OH, and $R_2$ can be H, $COCH_3$, or COH. In further aspects, the therapeutically effective amount adminstered can reduce cytotoxicity in the subject in need thereof as compared to a control. The therapeutically effective amount, in other aspects, can reduce the amount of reactive oxygen species in the subject in need thereof as compared to a control. In additional aspects, the therapeutically effective amount can reduce the oxidoreductase activity of the Nfa-1 protein as compared to a control. The organism having the Nfa-1 protein can be *N. fowleri*, *N. gruberi*, *Acanthamoeba hatchetti*, *A. healyi*, *A. polyphaga*, *A. rhysodes*, *A. astronyxis*, *A. divionensis*, *A. castellanii*, *Entamoeba histolytica*, *E. invadens*, *E. dispar*, *Balamuthia mandrillaris*, *Sappinia diploidea*, *Pyrococcus furiosus*, *Clostridium acetobutylicum*, *Desulfovibrio vulgaris*, *Burkholderia pseudomallei*, *Desulfurococcus mucosus*, *Methanococcus jannaschii*, *Riftia pachyptila*, *Phascolopsis gouldii*, *Periserrula leucophryna*, *Perinereis aibuhitensis*, *Theromyzon tessulatum*, *Hirudo medicinalis*, or *Themiste zostericola*. In some aspects of the method, the compound of Formula VI can be a compound according to Formula VII, Formula VIII, Formula IX, Formula X or a derivative of any of the foregoing compounds.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 5 demonstrates an alignment of *N. fowleri* Nfa-1 and an *Acanthamoeba castellanii* protein (Gen Bank Accession No. XP_004356500.1) with an Nfa-1 hemerythrin-like domain. The asterik (*) indicates amino acids that make up the Fe-oxygen binding site of three-dimensional (3-D) protein, of which a model is shown in FIG. 6A-6B.

FIG. 8 shows a table that summarizes the catalytic rates ($k_{cat}$), substrate affinities ($K_m$), catalytic efficiencies ($k_{cat}/K_m$), and maximum enzyme activities ($V_{max}$) of the *Naegleria fowleri* Nfa-1 hemerythrin enzyme as determined from the enzyme kinetic assay of FIG. 7A-7B.

FIGS. 12A-12B show the amino acid sequence (SEQ ID NO: 3) (FIG. 12A) and the genomic DNA sequence (SEQ ID NO: 4) (FIG. 12B) for N. fowleri Nfa-1. The underlined amino acids (FIG. 12A) and nucleotides (FIG. 12B) correspond to the Nfa-1 Fe-oxygen binding site as demonstrated in FIGS. 3, 5, and 6A-6B. The first Met in SEQ ID NO: 3 corresponds to the first three nucleotides in SEQ ID NO: 4 (the "start" codon). The last three nucleotides ("TAA") of SEQ ID NO: 4 correspond to the "stop" codon and thus do not have a corresponding amino acid in SEQ ID NO: 3.

DETAILED DESCRIPTION

Figure 1:
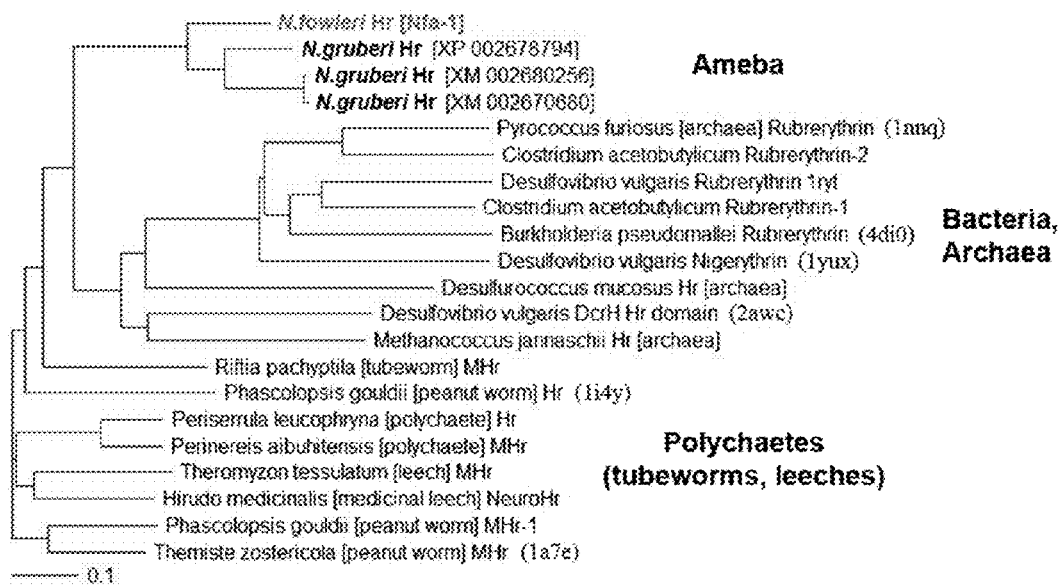
FIG. 1 shows a phylogram of *N. fowleri* Nfa-1 Hemerythrin (Hr) homologues in amoebae, bacteria, archaea and polychaetes for which genes were present in the NCBI GeneBank database as of the filing date of U.S. Provisional application. Amino acid sequences of hemerythrin-related proteins from *Naegleria* amoeba, bacteria, archaea, and polychaete worms were aligned using the ClustalW2 program.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

DEFINITIONS

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

As used herein, "about," "approximately," and the like, when used in connection with a numerical variable, generally refers to the value of the variable and to all values of the variable that are within the experimental error (e.g., within the 95% confidence interval for the mean) or within +1-10% of the indicated value, whichever is greater.

As used herein, "control" or "suitable control" is an alternative subject or sample used in an experiment for comparison purposes and included to minimize or distinguish the effect of variables other than an independent variable. A "control" can be positive or negative. A "control" as used herein refers to a control that will allow determination of a response to a compound, formulation, or treatment regimen described herein. "Control" includes a level of a physiologic characteristic or other parameter in a subject to be treated before administration of a compound or formulation described herein or before a treatment regimen. "Control" includes a pre-made standard or a range of values pre-determined to represent a normal level of the parameter being measured in a subject.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "purified" is used in reference to a nucleic acid sequence, peptide, or polypeptide or other compound that has increased purity relative to the natural environment or the environment in which it was produced in.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "therapeutic" refers to treating or curing a disease or condition.

As used herein, "preventative" refers to hindering or stopping a disease or condition before it occurs in a subject or while the disease or condition is still in the sub-clinical phase.

As used herein, "separated" refers to the state of being physically divided from the original source or population such that the separated compound, agent, particle, chemical compound, or molecule can no longer be considered part of the original source or population.

As used herein, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "chemotherapeutic agent" or "chemotherapeutic" refer to a therapeutic agent utilized to prevent or treat cancer.

As used herein, "dose," "unit dose," or "dosage" refers to physically discrete units suitable for use in a subject, each unit containing a predetermined quantity of the Nfa-1 inhibitor, derivative thereof, or formulation thereof calculated to produce the desired response or responses in association with its administration.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "specific binding partner" or "binding partner" is a compound or molecule to which a second compound or molecule binds with a higher affinity than all other molecules or compounds.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein "immunomodulator," refers to an agent, such as a therapeutic agent, which is capable of modulating or regulating one or more immune function or response.

As used herein, "differentially expressed," refers to the differential production of RNA, including, but not limited to, mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "variant" refers to a polypeptide that differs from a reference polypeptide or compound, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. A typical variant of a compound can be a derivative or analogue thereof.

As used herein, "functional variant" refers to a variant of a protein, polypeptide, molecule or compound (e.g., a variant of folic acid or a folic acid receptor protein) that can perform the same functions or activities as the original protein or polypeptide, although not necessarily at the same level (e.g., the variant may have enhanced, reduced or changed functionality, so long as it retains the basic function).

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "wild-type" is the typical form of an organism, variety, strain, gene, protein, or characteristic as it occurs in nature, as distinguished from mutant forms that may result from selective breeding or transformation with a transgene.

As used herein "induces," "inducing," or "induced" refers to activating or stimulating a process or pathway within a cell, such as endocytosis.

As used herein "heterogeneous" refers to a population of molecules, including nanoparticles, proteins, and polypeptides, or a population of subunits of a molecule that contains at least 2 molecules or subunits that are different from one another.

As used herein "homogenous" refers to a population of molecules, including nanoparticles, proteins, and polypeptides, or a population of subunits of a molecule in which all the molecules or subunits are identical to one another.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "administering" refers to an administration that is oral, topical, intravenous, subcutaneous, transcutaneous, transdermal, intramuscular, intracranial, intrajoint, parenteral, intra-arteriole, intradermal, intraventricular, intracranial, intraperitoneal, intralesional, intranasal, rectal, vaginal, intraurethral, by inhalation, or via an implanted reservoir. The term "parenteral" includes subcutaneous, intravenous, intramuscular, intra-articular, intrasynovial, intrasternal, intrathecal, intrahepatic, intralesional, and intracranial injections or infusion techniques.

As used herein, "composition" refers to a combination of an active agent(s) and another compound or composition, inert (for example, a detectable agent or label) or active, such as an adjuvant.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl) amino, carbamoyl, ($C_1$-$C_6$ alkyl)carbonyl, ($C_1$-$C_6$ alkoxy) carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl) sulfonyl, and arylsulfonyl. The groups listed above as suitable substituents are as defined hereinafter except that a suitable substituent may not be further optionally substituted.

As used herein, "optically substituted" indicates that a group may be unsubstituted or substituted with one or more substituents as defined herein.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, and $C_3$-$C_{30}$ for branched chains). In other embodiments, a straight chain or branched chain alkyl contains 20 or fewer, 15 or fewer, or 10 or fewer carbon atoms in its backbone. Likewise, in some embodiments cycloalkyls have 3-10 carbon atoms in their ring structure. In some of these embodiments, the cycloalkyl have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O—alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

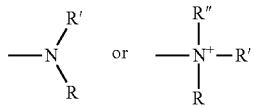

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

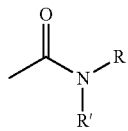

wherein R and R' are as defined above.

As used herein, "Aryl" refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

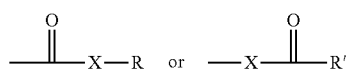

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium.

As used herein, the term "nitro" refers to —NO$_2$; the term "halogen" designates —F, —Cl, —Br, or —I; the term "sulfhydryl" refers to —SH; the term "hydroxyl" refers to —OH; and the term "sulfonyl" refers to —SO$_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "therapeutically effective amount" refers to the amount of an Nfa-1 inhibitor, derivative thereof, pharmaceutical formulation thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of Nfa-1 inhibitor, derivative thereof, or pharmaceutical formulation thereof that, when administered alone or co-administered with a secondary agent, is sufficient to prevent development of, reduce or alleviate to some extent, one or more of the symptoms of an infection of an organism having an Nfa-1 protein. "Therapeutically effect amount" includes that amount of Nfa-1 inhibitor, derivative thereof, or pharmaceutical formulation thereof that, when administered alone or co-administered with a secondary agent, is sufficient to reduce cytotoxicity in a subject suspected of being infected with or infected with an organism having an Nfa-1 protein as compared to a control. "Therapeutically effect amount" includes that amount of Nfa-1 inhibitor, derivative thereof, or pharmaceutical formulation thereof that, when administered alone or co-administered with a secondary agent, is sufficient to reduce reactive oxygen species (ROS) in a subject or cell thereof suspected of being infected with or infected with an organism having an Nfa-1 protein as compared to a control. "Therapeutically effect amount" includes that amount of Nfa-1 inhibitor, derivative thereof, or pharmaceutical formulation thereof that, when administered alone or co-administered with a secondary agent, is sufficient to reduce Nfa-1 oxidoreductase activity of Nfa-1 in a subject suspected of being infected with or infected with an organism having an Nfa-1 protein as compared to a control. The therapeutically effective amount will vary depending on the exact chemical structure of the Nfa-1 inhibitor, the exact organism having an Nfa-1 protein causing the infection in the subject, the severity and/or type of the infection or other disease, disorder, syndrome, or symptom thereof being treated, the route of administration, the time of administration, the rate of excretion, the drug combination, the judgment of the treating physician, the dosage form, and the age, weight, general health, sex and/or diet of the subject to be treated.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

As used herein, "treat," "treating," "treatment" and grammatical variations thereof as used herein include partially or completely delaying, alleviating, mitigating or reducing the intensity of one or more attendant symptoms of a disorder or condition such as an atypical protein kinase C enzyme abnormality and/or alleviating, mitigating or impeding one or more causes of a disorder or condition such as an atypical protein kinase C enzyme abnormality. Treatments according to the embodiments disclosed herein may be applied preventively, prophylactically, palliatively or remedially. In some instances, the terms "treat," "treating," "treatment" and grammatical variations thereof include partially or completely reducing a condition or symptom associated with, for example, an atypical protein kinase C enzyme abnormality as compared with prior to treatment of the subject or as compared with the incidence of such condition or symptom in a general or study population.

As used herein, "identity," is a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch (J. Mol. Biol., 1970, 48: 443-453) algorithm (e.g., NBLAST, and XBLAST). The default parameters are used to determine the identity for the polypeptides of the present disclosure.

As used herein, "structural analogue" refers to a compound, molecule, protein, and the like, that has a structure similar to that of another compound, but is different in one aspect, such as an atom or functional group.

As used herein, "functional analogue" refers to a compound molecule, nucleotide sequence, protein, and the like, that has the same or similar physical, chemical, biochemical, pharmacological propertieis, or elicit the same effect as another molecule, protein, and the like. In some embodiments, functional analogues are also structural analogues. In other embodiments, functional analogues are not structural analogues.

As used herein, "analogue" refers to both the terms "structural analogue" and "functional analogue."

As used herein, "heterologue" refers to compounds, molecules, nucleotide sequences (including genes), and polypeptide sequences (including peptides and proteins) that are different in both activity (function) and sequence or chemical structure.

As used herein, "homologue" refers to a polypeptide sequence that shares a threshold level of similarly and/or identity as determined by alignment of matching amino acids. Two or more polypeptides determined to be homologues are said to be homologues. Homology is a qualitative term that describes the relationship between polypeptide sequences that is based upon the quantitative similarity.

As used herein, "paralog" refers to a homologue produced via gene duplication of a gene. In other words, paralogs are homologues that result form divergent evolution from a common ancesteral gene.

As used herein, "orthologs" refers to homologues produced by speciation followed by divergence of sequence but not activity in separate species. When speciation follows duplication and one homologue sorts with one species and the other copy sorts with the other species, subsequent divergence of the duplicated sequence is associated with one or the other species. Such species specific homologues are referred to herein as orthologs.

As used herein, "xenologs" are homologues resulting from horizontal gene transfer.

As used herein, "similarity" is a quantitative term that defines the degree of sequence match between two compared polypeptide sequences.

As used herein, "Nfa-1 containing organism" and "organism having an Nfa-1 protein" refers to an organism that contains or expresses an Nfa-1 protein as defined herein.

As used herein "Nfa-1 protein" refers to and includes *N. fowleri* Nfa-1 and any functional and structural analogues, homologues, paralogs, orthologs, xenologs of *N. fowleri* Nfa-1. "Nfa-1 protein" also includes any functional and structural analogues, homologues, paralogs, orthologs, xenologs of the Fe-oxygen binding site *N. fowleri* Nfa-1. The threshold for considering a protein an *N. fowleri* Nfa-1 homologue is an identity of 25% or higher and a similarity of 30% or higher at the amino acid level.

Discussion

Pathogenic and opportunistic free-living amoebae, such as *Acanthanoeba* ssp. *Balamuthia mandrillaris, Sappinia diploidea*, and *Naegleria fowleri*, are protists that occur world-wide and can cause serious and sometimes fatal infections in humans and other animals. *Acanthanoeba* ssp. and *B. mandrillaris* cause granulomatous amoebic encephalitis (GAE), which is insidious, chronic, and mostly fatal. *Acanthanoeba* ssp. and *B. mandrillaris* most often cause disease in immunocompromised or otherwise debilitated individuals. In addition to causing central nervous system infections, *Acanthanoeba* ssp. can cause vision-threatening keratitis. Both *Acanthanoeba* ssp. and *B. mandrillaris* can cause infection of the lungs and skin. *S. diploidea*, which is found in soil contaminated with fecal matter from elk, bison, and cattle, can cause encephalitis in healthy individuals. *N. fowleri* causes an acute necrotizing and hemorrhagic meningoencephalitis (PAM), which results in death in over 95% of cases.

While alarmingly devastating in nature, infections from free-living amoebae are rare and typically affect fewer than 200,000 people. Given the rarity of pathogenic amoebae diseases, little research and product development has gone into developing treatment. As such, no effective and efficient therapy exists for the treatment of pathogenic and opportunistic free-living amoebae, such as those described above. With that said, described herein are compounds, pharmaceutical formulations, and methods of using the compounds and pharmaceutical formulations to treat or prevent amoebae infection or symptom thereof in a subject infected with or suspected of being infected with an amoebae or other organism having an Nfa-1 protein.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Nfa-1 Inhibitors and Formulations Thereof

Nfa-1 Inhibitors

The pathology of some amoebic infections include the generation of reactive oxygen species (ROS), which can contribute to the cytotoxicity observed in some of these diseases. It has been known that cells infected with an amoeba (e.g. *N. fowleri*) have increased ROS. NADPH oxidase (NOX) of the host cell has been demonstrated to be involved in the generation of ROS in cells infected with amoeba. However as demonstrated herein, host-cell NOX is not the only source for ROS in amoebae infected cells.

Nfa-1 is a protein recently identified to be a virulence factor in *N. fowleri*. See Kang et. al. 2005. Clin. Diagn. Lab. Immunol 12:873-876 and Jeong et al. 2005. Infect. Immun. 73:4098-4105. Nfa-1 belongs to the Fe-binding hemerythrin protein family based on its amino acid sequence, but no biochemical characterization or enzymatic function has been identified. Until now, it was only known that Nfa-1 appears to play a role in the cell contact mechanism of *N. fowleri* (Id.), which was thought to play a role in cytotoxic effect of the organism. As shown in the Examples herein, amoebic Nfa-1 has NAD(P)H-dependent oxidoreductase activity and therefore can contribute to the production of ROS in infected cells. Therefore, Nfa-1 can play a role in the cytotoxicity observed in amoebic infections and other organisms having an Nfa-1 protein.

The compositions described herein can alter Nfa-1 oxidoreductase activity. In some embodiments, the compounds described herein reduce and/or inhibit Nfa-1 oxidoreductase activity. In some embodiments, the compositions described herein can reduce the amount of ROS in a subject or cell thereof infected with an organism having an Nfa-1 protein. In other embodiments, the compositions described herein can reduce cytotoxicity in a subject infected or suspected of being infected with an organism having an Nfa-1 protein. The compositions described herein can be made using methods generally known in the art.

The compositions can have a formula according to Formula I:

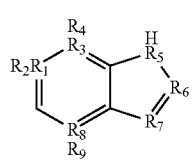

Formula I where $R_1$ can be N or C, $R_2$ can be O or H, $R_3$ can be N or C, $R_4$ can be H, OH, O, or S, can be $R_5$ is N or C, $R_6$ can be N or C, $R_7$ can be N or C, $R_8$ can be N or C, and $R_9$ can be H or O.

In other embodiments, the composition can have a formula according to any one of Formula II, Formula III, Formula IV, or Formula V:

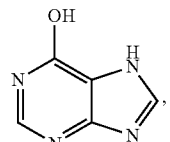

Formula II

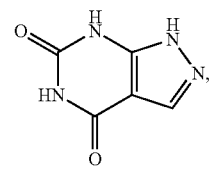

Formula III

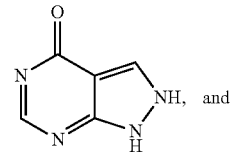

Formula IV

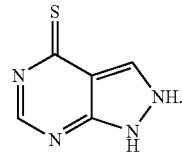

Formula V

In further embodiments, the compositions can be suitable derivatives of any one of Formula I, Formula II, Formula III, Formula IV, or Formula V. Suitable derivatives can be derivatives that alter Nfa-1 oxidoreductase activity. In some embodiments, the suitable derivatives can reduce ROS in a subject or cell thereof infected with or suspected of being infected with an organism having an Nfa-1 protein. In other embodiments, the suitable derivatives can reduce cytotoxicity in a subject or infected with or suspected of being infected with an organism having an Nfa-1 protein.

The compositions can also have a formula according to Formula VI:

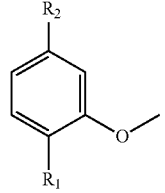

Formula VI where $R_1$ can be H or OH and $R_2$ can be H, $COCH_3$, or COH.

In some embodiments the composition can have a formula according to Formula VII, Formula VIII, Formula IX, or Formula X.

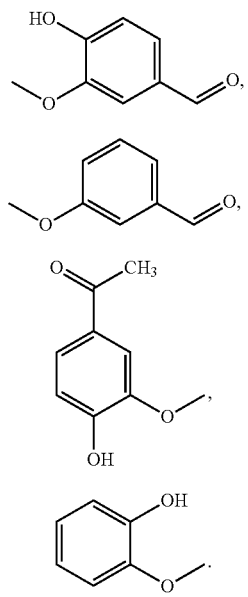

Formula VII

Formula VIII

Formula IX

Formula X

In further embodiments, the compositions can be suitable derivatives of any one of Formula VI, Formula VII, Formula VIII, Formula IX, or Formula X. Suitable derivatives can be derivatives that alter Nfa-1 oxidoreductase activity. In some embodiments, the suitable derivatives can reduce ROS in a subject or cell thereof infected with or suspected of being infected with an organism having an Nfa-1 protein. In other embodiments, the suitable derivatives can reduce cytotoxicity in a subject or infected with or suspected of being infected with an organism having an Nfa-1 protein.

Pharmaceutical Formulations

The Nfa-1 inhibitors described herein can be provided to a subject alone or as an ingredient, such as an active ingredient, in a pharmaceutical formulation. As such, also described herein are pharmaceutical formulations containing one or more of the Nfa-1 inhibitors described herein. In some embodiments, the pharmaceutical formulations contain a therapeutically effective amount of one or more Nfa-1 inhibitors described herein.

The pharmaceutical formulations can be administered to a subject in need thereof. In some embodiments, the subject in need thereof can be suspected of being infected with an organism having an Nfa-1 protein. In some embodiments, the organism can be *N. fowleri*, *N. gruberi*, *Acanthamoeba* ("*A.*") *hatchetti*, *A. healyi*, *A. polyphaga*, *A. rhysodes*, *A. astronyxis*, *A. divionensis*, *A. castellanii*, *Entamoeba histolytica*, *E. invadens*, *E. dispar*, *Balamuthia mandrillaris*, *Sappinia diploidea*, *Pyrococcus furiosus*, *Clostridium acetobutylicum*, *Desulfovibrio vulgaris*, *Burkholderia pseudomallei*, *Desulfurococcus mucosus*, *Methanococcus jannaschii*, *Riftia pachyptila*, *Phascolopsis gouldii*, *Periserrula leucophryna*, *Perinereis aibuhitensis*, *Theromyzon tessulatum*, *Hirudo medicinalis*, or *Themiste zostericola*. In other embodiments the subject in need thereof can be infected with or be suspected of being infected with an organism having an Nfa-1 protein. In other embodiments, the Nfa-1 inhibitors can be used in the manufacture of a medicament for the treatment or prevention of an infection or symptom thereof caused by an organism having an Nfa-1 protein.

Pharmaceutically Acceptable Carriers and Auxiliary Ingredients and Agents

The pharmaceutical formulations containing a therapeutically effective amount of a Nfa-1 inhibitor described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of the Nfa-1 inhibitors, the pharmaceutical formulation can also include an effective amount of auxiliary active agents, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Effective Amounts of the Nfa-1 Inhibitors and Auxiliary Agents

The pharmaceutical formulations can contain a therapeutically effective amount of an Nfa-1 inhibitor and/or a therapeutically effective amount of an auxiliary agent. In some embodiments, the therapeutically effective amount of the Nfa-1 inhibitor can range from about 0.01 mg/kg to about 20 mg/kg. In some embodiments, the therapeutically effective mount of the Nfa-1 inhibitor can range from about 1 mg/kg to about 6 mg/kg.

In embodiments where there is an auxiliary active agent contained in the pharmaceutical formulation in addition to the Nfa-1 inhibitor, the therapeutically effective amount of the auxiliary active agent will vary depending on the auxiliary active agent. In some embodiments, the effective amount of the auxiliary active agent ranges from 0.001 micrograms to about 1 milligrams. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The auxiliary active agent can be included in the pharmaceutical formulation or can exist as a stand-alone compound or pharmaceutical formulation that is administered contemporaneously or sequentially with the conjugate compound, derivative thereof or pharmaceutical formulation thereof. In embodiments where the auxiliary active agent is a stand-alone compound or pharmaceutical formulation, the therapeutically effective amount of the auxiliary active agent can vary depending on the auxiliary active agent used. In some of these embodiments, the therapeutically effective amount of the auxiliary active agent can range from 0.001 micrograms to about 1000 grams. In other embodiments, the therapeutically effective amount of the auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the auxiliary active agent can range from about 1% w/w to about 50% w/w of the total auxiliary active agent pharmaceutical formulation. In additional embodiments, the therapeutically effective amount of the auxiliary active agent can range from about 1% v/v to about 50% v/v of the total pharmaceutical formulation. In still other embodiments, the therapeutically effective amount of the auxiliary active agent can range from about 1% w/v to about 50% w/v of the total auxiliary agent pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, intraurethral, parenteral, intracranial, subcutaneous, intramuscular, intravenous, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. In some embodiments, the oral dosage form can contain about 100 mg, about 200 mg, or about 300 mg of a pharmaceutical formulation containing a therapeutically effective amount or an appropriate fraction thereof of an Nfa-1 inhibitor. The oral dosage form can be administered to a subject in need thereof. In some embodiments, this is a subject infected with or suspected of being infected with an organism having an Nfa-1 protein.

Where appropriate, the dosage forms described herein can be microencapsulated. The dosage form can also be prepared to prolong or sustain the release of any ingredient. In some embodiments, the Nfa-1 inhibitor is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the Nfa-1 inhibitor, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the Nfa-1 inhibitor, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of a Nfa-1 inhibitor, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a conjugate compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulations. In addition to the Nfa-1 inhibitor, auxiliary active ingredient, and/or pharmaceutically acceptable salt thereof, such a dosage form can contain a powder base such as lactose, glucose, trehalose, manitol, and/or starch. In some of these embodiments, the conjugate compund, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for injection can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of an Nfa-1 inhibitor per unit dose. In an embodiment, the predetermined amount of the Nfa-1 inhibitor is a therapeutically effective amount of the Nfa-1 inhibitor to treat, prevent, or mitigate the symptoms of an infection with an organism having an Nfa-1 protein. In other embodiments, the predetermined amount of the Nfa-1 inhibitor is an appropriate fraction of the effective amount of the active ingredient. Such unit doses may therefore be administered once or more than once a day. Such pharmaceutical formulations may be prepared by any of the methods well known in the art.

Methods of Using the Nfa-1 Inhibitors and Formulations Thereof

The Nfa-1 Inhibitors and pharmaceutical formulations thereof described herein can be used for treatment or prevention of a disease, disorder, syndrome, or a symptom thereof. In some embodiments, the Nfa-1 Inhibitor can be used to treat a subject infected with or suspected of being infected with an organism having an Nfa-1 protein. In some embodiments, the organism having an Nfa-1 protein can be *N. fowleri, N. gruberi, Acanthamoeba ("A.") hatchetti, A. healyi, A. polyphaga, A. rhysodes, A. astronyxis, A. divionensis, A. castellanii, Entamoeba histolytica, E. invadens, E. dispar, Balamuthia mandrillaris, Sappinia diploidea, Pyrococcus furiosus, Clostridium acetobutylicum, Desulfovibrio vulgaris, Burkholderia pseudomallei, Desulfurococcus mucosus, Methanococcus jannaschii, Riftia pachyptila, Phascolopsis gouldii, Periserrula leucophryna, Perinereis aibuhitensis, Theromyzon tessulatum, Hirudo medicinalis*, or *Themiste zostericola.*

An amount of the Nfa-1 inhibitor and pharmaceutical formulations thereof, described herein can be administered to a subject in need thereof one or more times per day, week, month, or year. In some embodiments, the subject has one or more symptoms of a disease, condition, or syndrome. In some embodiments, the Nfa-1 Inhibitor can be used to treat a subject infected with or suspected of being infected with an organism having an Nfa-1 protein. In some embodiments, the organism having an Nfa-1 protein can be *N. fowleri, N. gruberi, Acanthamoeba hatchetti, A. healyi, A. polyphaga, A. rhysodes, A. astronyxis, A. divionensis, A. castellanii, Entamoeba histolytica, E. invadens, E. dispar, Balamuthia mandrillaris, Sappinia diploidea, Pyrococcus furiosus, Clostridium acetobutylicum, Desulfovibrio vulgaris, Burkholderia pseudomallei, Desulfurococcus mucosus, Methanococcus jannaschii, Riftia pachyptila, Phascolopsis gouldii, Periserrula leucophryna, Perinereis aibuhitensis, Theromyzon tessulatum, Hirudo medicinalis*, or *Themiste zostericola*

In some embodiments, the amount administered can be the therapeutically effective amount of the Nfa-1 inhibitor or pharmaceutical formulations thereof. For example, the Nfa-1 inhibitor or pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the Nfa-1 inhibitors or pharmaceutical formulations thereof are administered one or more times per month, such as 1 to 5 times per month. In still further embodiments, the Nfa-1 inhibitor or pharmaceutical formulations thereof are administered one or more times per year, such as 1 to 11 times per year.

The Nfa-1 inhibitor or pharmaceutical formulations thereof can be co-administered with a secondary agent by any convenient route. The secondary agent is a separate compound and/or formulation from the Nfa-1 inhibitor or pharmaceutical formulation thereof. The secondary agent can be administered simultaneously with the Nfa-1 inhibitor or pharmaceutical formulation thereof or sequentially with the Nfa-1 inhibitor or pharmaceutical formulation thereof. The secondary agent can have an additive or synergistic effect to the Nfa-1 inhibitor or pharmaceutical formulation thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-78, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase Erwinia chrysanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where the Nfa-1 inhibitor or pharmaceutical formulation thereof is simultaneous co-administered with a secondary agent, the Nfa-1 inhibitor or pharmaceutical formulation thereof is administered to the subject at substantially the same time as the secondary agent. As used in this context "substantially the same time" refers to administration of the Nfa-1 inhibitor or pharmaceutical formulation thereof and a secondary agent where the period of time between administration of the Nfa-1 inhibitor or pharmaceutical formulation thereof and a secondary agent is between 0 and 10 minutes.

In embodiments where the Nfa-1 inhibitor or pharmaceutical formulation thereof are sequentially co-administered with a secondary agent, the Nfa-1 inhibitor or pharmaceutical formulation thereof can be administered first followed by administration of the secondary agent after a period of time. In other embodiments where the Nfa-1 inhibitor or pharmaceutical formulation thereof are sequentially co-administered with a secondary agent, the secondary agent can be administered first followed by administration of the Nfa-1 inhibitor or pharmaceutical formulation thereof after a period of time. In any embodiment, the period of time can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the Nfa-1 inhibitors, pharmaceuticals formulations thereof, and secondary agents described herein can be administered in an amount ranging from about 0.01 mg to about 10 g per day, as calculated as the free or unsalted compounds or pharmaceutical formulations. The amount of Nfa-1 inhibitors, pharmaceuticals formulations thereof, and secondary agents described herein can be administered in an amount ranging from about 0.01 µM to about 10 µM per day.

Kits Containing the Nfa-1 Inhibitors and Formulations Thereof

The Nfa-1 inhibitors and pharmaceuticals formulations thereof described herein can be presented as a combination kit. As used herein, the terms "combination kit" or "kit of parts" refers to the Nfa-1 inhibitors or pharmaceuticals formulations thereof described herein and additional components that are used to package, sell, market, deliver, and/or administer the combination of elements or a single element, such as the active ingredient, contained therein. Such additional components include, but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the Nfa-1 inhibitors or pharmaceuticals formulations thereof, pharmaceutical formulations thereof, and/or other auxiliary agent contained therein, safety information regarding the content of the Nfa-1 inhibitors, pharmaceuticals formulations thereof, pharmaceutical formulations thereof, auxiliary agent, or secondary contained therein, information regarding the dosages, indications for use, and/or recommended treatment regimen(s) for the Nfa-1 inhibitors, pharmaceuticals formulations thereof, and/or other auxiliary or secondary agent contained therein. In some embodiments, the instructions provide directions for administering the compounds, pharmaceutical formulations, or salts thereof to a subject infected with or suspected of being infected with an organism having an Nfa-1 protein. In some embodiments, organism having an Nfa-1 protein can be *N. fowleri*, *N. gruberi*, *Acanthamoeba hatchetti*, *A. healyi*, *A. polyphaga*, *A. rhysodes*, *A. astronyxis*, *A. divionensis*, *A. castellanii*, *Entamoeba histolytica*, *E. invadens*, *E. dispar*, *Balamuthia mandrillaris*, *Sappinia diploidea*, *Pyrococcus furiosus*, *Clostridium acetobutylicum*, *Desulfovibrio vulgaris*, *Burkholderia pseudomallei*, *Desulfurococcus mucosus*, *Methanococcus jannaschii*, *Riftia pachyptila*, *Phascolopsis gouldii*, *Periserrula leucophryna*, *Perinereis aibuhitensis*, *Theromyzon tessulatum*, *Hirudo medicinalis*, or *Themiste zostericola*.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Phylogram Analysis of Nfa-1 Proteins

Figure 2:
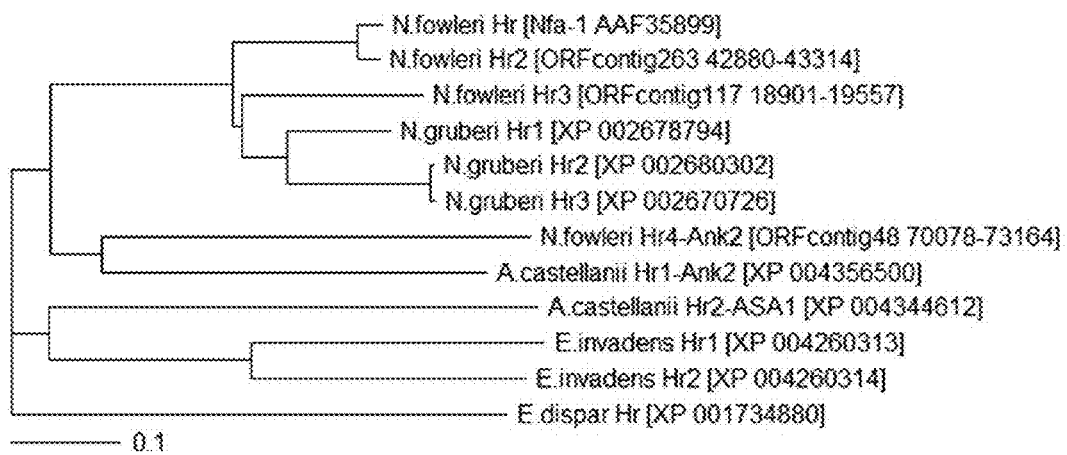
FIG. 2 shows a phylogram of *N. fowleri* Nfa-1 Hemerythrin (Hr) and related proteins in other amoebae with sequenced genomes. Amino acid sequences of hemerythrin-related proteins from *Naegleria* amoebae (*N. fowleri*, *N. gruberi*) and the pathogenic amoebae *Acanthamoeba* (*A. castellanii*) and *Entamoeba* (*E. invadens*, *E. dispar*) were aligned using the ClustalW2 program. Protein IDs and accession numbers are given in square brackets.

Amino acid sequences of hemerythrin-related proteins from various amoebae, bacteria, archaea, and polychaete worms with sequenced genomes were obtained from NCBI GenBank or AmoebaDB online databases. Alignment of amino acid sequences was completed using ClustalW2 and results were displayed as phylograms, which graphically demonstrates the identity relationship between the amino acid sequences observed. Representative phylograms are shown in FIGS. 1 and 2. As demonstrated in FIG. 1, *N. fowleri* Nfa-1 hemerythrin (Hr) had the closest homology to *N. gruberi* hemerythrins, followed by the Glade of bacterial and archaea Hr-related proteins.

Example 2

LIGPLOT Analysis of *N. fowleri* Nfa-1 Fe-Oxygen Protein-Ligand Interactions

Figure 3:
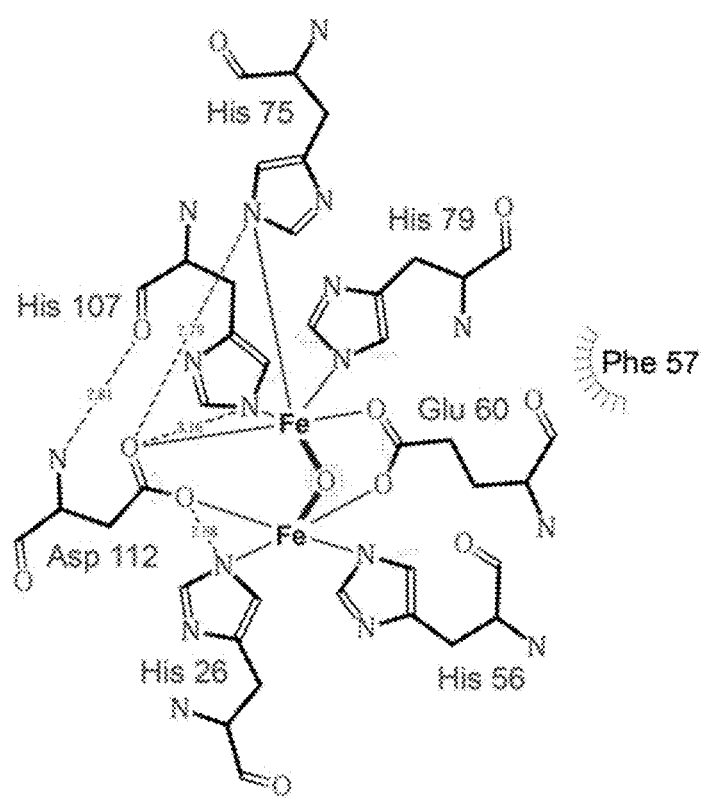
FIG. 3 demonstrates the results of a LIGPLOT analysis of *N. fowleri* Nfa-1 Fe-oxygen Protein ligand interactions. LIGPLOT analysis of *N. fowleri* Nfa-1 bound with two ferric (Fe) ions and oxygen was generated from the LIGPLOT and crystal structure of *P. gouldii* Hr (PDB: li4y at 1.8 Å). The Hr-Fe binding site was made of five histidine (His) residues and two acidic residues (glutamate, Glu60 and aspartate, Asp112) that form ionic bonds (in blue) with two Fe ions. Phenylalanine Phe57 forms hydrophobic interactions (depicted as eyelashes) that can stabilize the Fe binding pocket. Hydrogen bonds and their lengths in Angstrom (Å) are shown in red.

LIGPLOT of *N. fowleri* Nfa-1 bound with two ferric (Fe) ions and oxygen was generated from the LIGPLOT and crystal structure of *P. gouldii* Hr as provided in the online Protein Data Bank, PDBsum (PDBsum identification: "li4y" at 1.8 Å) (FIG. 3) following pairwise alignment of the *N. fowleri* Nfa-1 with the *P. gouldii* Hr amino acid sequence by pairwise BLAST (NCBI/BLAST/blastp suite), which allowed identification of the specific amino acids in *N. fowleri* Nfa-1 that correspond to the specific amino acids given in the *P. gouldii* Hr LIGPLOT in PDBsum. Hence the Hr-Fe binding site was observed to be composed of five histidine (His) residues and two acidic residues (glutamate, Glu60 and aspartate, Asp112) that form ionic bonds (in blue) with two Fe ions. Phenylalanine Phe57 forms hydrophobic interactions (depicted as eyelashes) that stabilize the Fe binding pocket. Hydrogen bonds and their apparent lengths in Angstrom (Å) are given in red (FIG. 3).

Example 3

Figure 4:
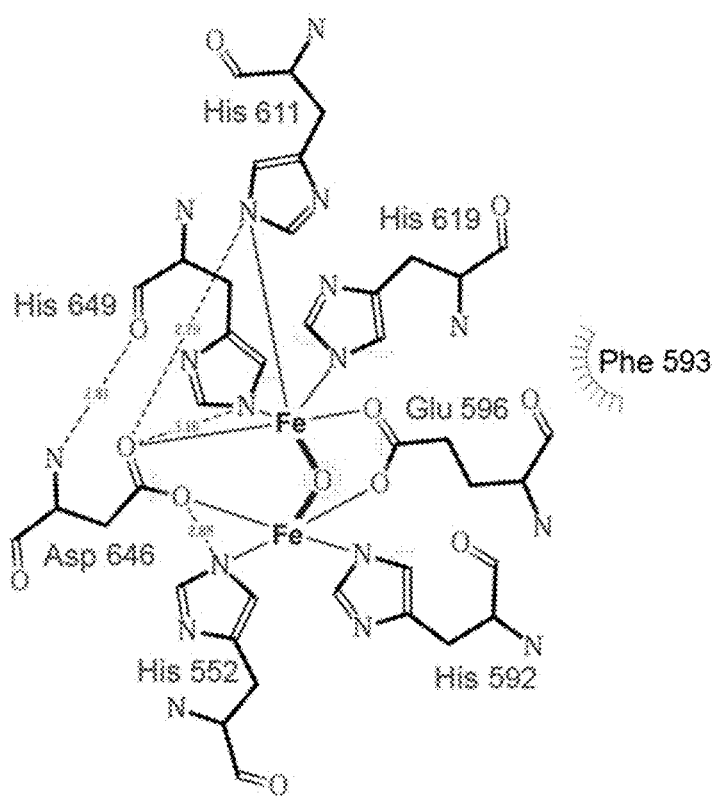
FIG. 4 demonstrates a LIGPLOT analysis of an *Acanthamoeba* protein with an Nfa-1 like Hemerythrin domain as determined by a BLAST search of *N. fowleri* Nfa-1 against *Acanthamoeba castellanii* (Gen Bank Accession No. XP_004356500.1).

Blast Search and Ligplot Analysis of *Acanthamoeba* Protein with Nfa-1 Like Hemerythrin Domain A BLAST search of the entire 119-amino acid *N. fowleri* Nfa-1 protein sequence against *Acanthamoeba* genes in GenBank was conducted. The BLAST search revealed an *Acanthamoeba castellanii* protein (XP_004356500.1) with an Nfa-1 hemerythrin-like domain that showed 32% (37/117) identity and 52% (61/117) similarity at the amino acid level with the whole *N. fowleri* homologue (FIG. 5). The LIGPLOT (FIG. 4) and BLAST (FIG. 5) analysis of the *Acanthamoeba* hemerythrin revealed 100% amino acid identity for the Fe-oxygen binding site of the enzyme with the *N. fowleri* Nfa-1 oxidase as highlighted and marked with an asterik (*) in FIG. 5 for the eight respective amino acids that form the binding site. This suggests that the putative (Gen Bank Accession No. XP_004356500.1) protein is an Nfa-1 homologue.

Example 4

Molecular Structure of *N. fowleri* Nfa-1 Hemerythrin

Figure 6A:
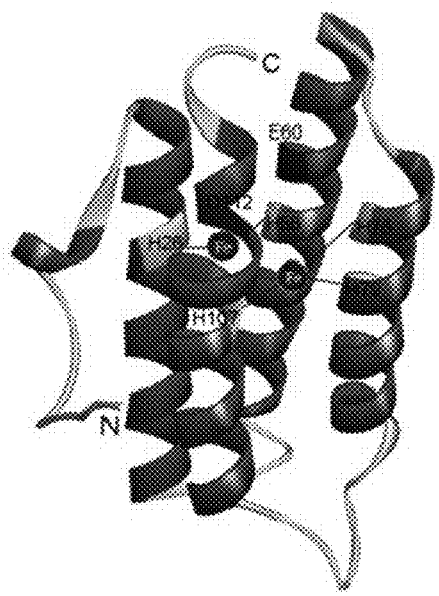
FIGS. 6A-6B demonstrate a side view (FIG. 6A) and a top view (FIG. 6B) of a 3-D ribbon diagram of *N. fowleri* Nfa-1 Hr. The labeled amino acids correspond to the (*) labeled amino acids of FIG. 5.
Figure 6B:
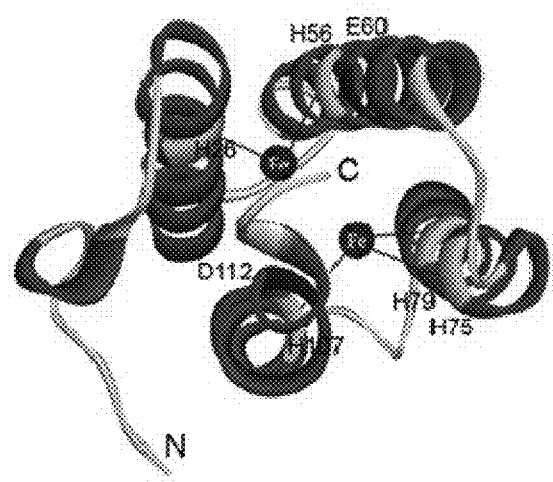

FIGS. 6A and 6B demonstrate a side view (FIG. 6A) and top view (FIG. 6B) of a ribbon diagram of *N. fowleri* Nfa-1 Hr. The predicted protein structure of Nfa-1 was modeled in silico using *Phascolopsis gouldii* Hr (PDB: 1i4y 1.8 Å) as template (QMEAN4 score of 0.69). For in silico modeling, amino acid sequences were pair-wise aligned with ClustalW2 followed by protein modeling in SWISS-MODEL with the molecular structure shown as solid ribbon model (FIGS. 6A and 6B). The five histidine (His) residues of the Fe iron binding site are shown in yellow and the two acidic residues glutamate Glu60 and aspartate Asp112 are marked in blue (FIGS. 6A and 6B). For clarity, only the ionic bonds between the five His residues and two Fe ions are shown (FIGS. 6A and 6B).

FIGS. 12A-12B show the amino acid sequence (SEQ ID NO: 3) (FIG. 12A) and the DNA sequence (SEQ ID NO: 4) (FIG. 12B for *N. fowleri* Nfa-1. The GenBank Accession No. for SEQ ID NO: 3 is AAF35899 and the GenBank Accession No. for SEQ ID NO: 4 is AF230370. The eight underlined amino acids (FIG. 12A) and nucleotides (FIG. 12B) correspond to the Nfa-1 Fe-oxygen binding site as demonstrated in FIGS. 3, 5, and 6A-6B. These are His26, His56, Phe57, Glu60, His75, His79, His107, Asp112 in SEQ ID NO: 3, where the first Met is considered amino acid 1 in the sequence. The first Met in SEQ ID NO: 3 corresponds to the first three nucleotides in SEQ ID NO: 4 (the "start" codon). The last three nucleotides ("TAA") of SEQ ID NO: 4 correspond to the "stop" codon and thus do not have a corresponding amino acid in SEQ ID NO: 3. Nucleotides (nt)76-78, nt166-168, nt169-171, nt178-180, nt223-225, nt235-237, nt319-321, nt334-336 in SEQ ID NO: 4 correspond to the codons for the eight amino acids that correspond to the Fe-oxygen binding site in SEQ ID NO: 3 previously discussed.

Example 5

Nfa-1 Oxidoreductase Activity, Enzyme Kinetics, and Pharmacological Inhibition Assay Cloning of *N. fowleri* Nfa-1 Hemerythrin and Production of Recombinant Nfa-1 Enzyme.

The *N. fowleri* Nfa-1 gene (360 bp, Gen Bank Accession No. AF230370) was amplified by PCR from genomic *N. fowleri* DNA using PCR primers that included the Nde1 and Sap1 restriction enzyme sites for subsequent cloning into the Nde1 and Sap1 sites of the bacterial expression vector pTwin1 (forward primer with Nde1 site underlined; ATG start codon is indicated in bold:

SEQ ID NO: 1
5'-TAGCTA<u>CATATG</u>GCCACTACTATTCCATCACCATTC-3', reverse primer with Sap1 site underlined:

SEQ ID NO: 2
5'-CAGTAT<u>GCTCTT</u>CTGCAAAGCACTCCCTTGTACTTCATATCAG-3'), which contained a thiol-inducible intein protease fused to a chitin-binding domain. Recombinant Nfa-1 protein was produced in *E. coli* and purified by chitin-agarose chromatography followed by cleavage and elution of the purified Nfa-1 protein by 40 mM dithiothreitol (DTT) and subsequent size-exclusion chromatography purification.

Measurement of Nfa-1 Hemerythrin Enzyme Kinetics and Pharmacological Inhibition Assays.

Enzymatic oxidase activity, kinetics and pharmacological drug inhibition assays of recombinant *N. fowleri* Nfa-1 hemerythrin were determined in vitro using NADH or NADPH as the substrate and electron donor and ferricyanide as electron acceptor. Various drugs and inhibitors specific for xanthine oxidase-like enzymes, NAD(P)H oxidases, or NADH peroxidase were included in the pharmacological inhibition assays.

Initial-Rate Enzyme Kinetics of *N. fowleri* Nfa-1 Hemerythrin Using NADH or NADPH as Substrates.

Figure 7A:
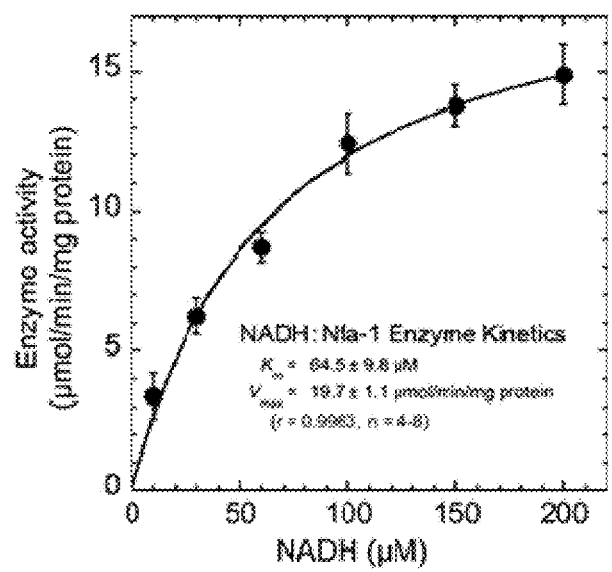
FIGS. 7A-7B show graphs demonstrating the results of an enzyme activity assay performed to determine enzyme kinetics of *N. fowleri* Nfa-1 Hr when NADH (FIG. 7A) or NADPH (FIG. 7B) is used as a substrate.
Figure 7B:
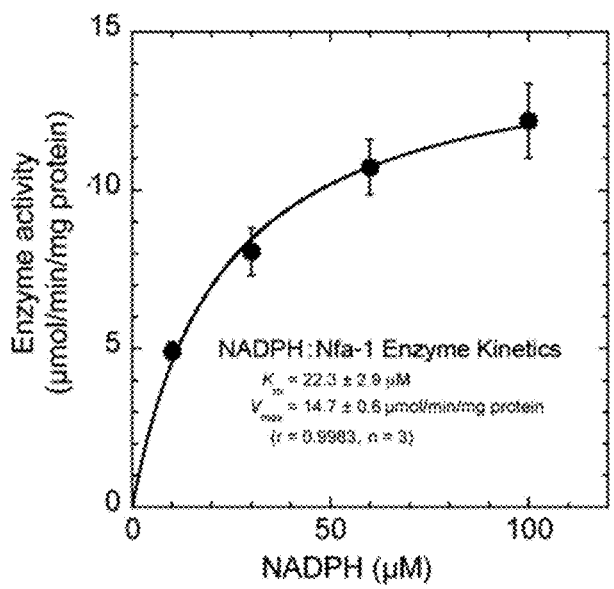

Enzyme kinetics were determined using NADH or NADPH at 10-200 µM concentration as electron donor and ferricyanide (200 µM) as electron acceptor for initial-rate enzyme kinetics of 40 sec at 23° C. Apparent $K_m$ values of 64.5 µM (NADH) and 22.3 µM (NADPH), and apparent $k_{cat}$ values of 4.4/sec (NADH) and 3.3/sec (NADPH) were determined by Michaelis-Menten kinetics analysis. Results of the Nfa-1 enzyme activity assays are demonstrated in FIGS. 7A-7B and FIG. 8.

Inhibitor Profile and Pharmacology of *N. fowleri* Nfa-1 Oxidase In Vitro.

Figure 9:
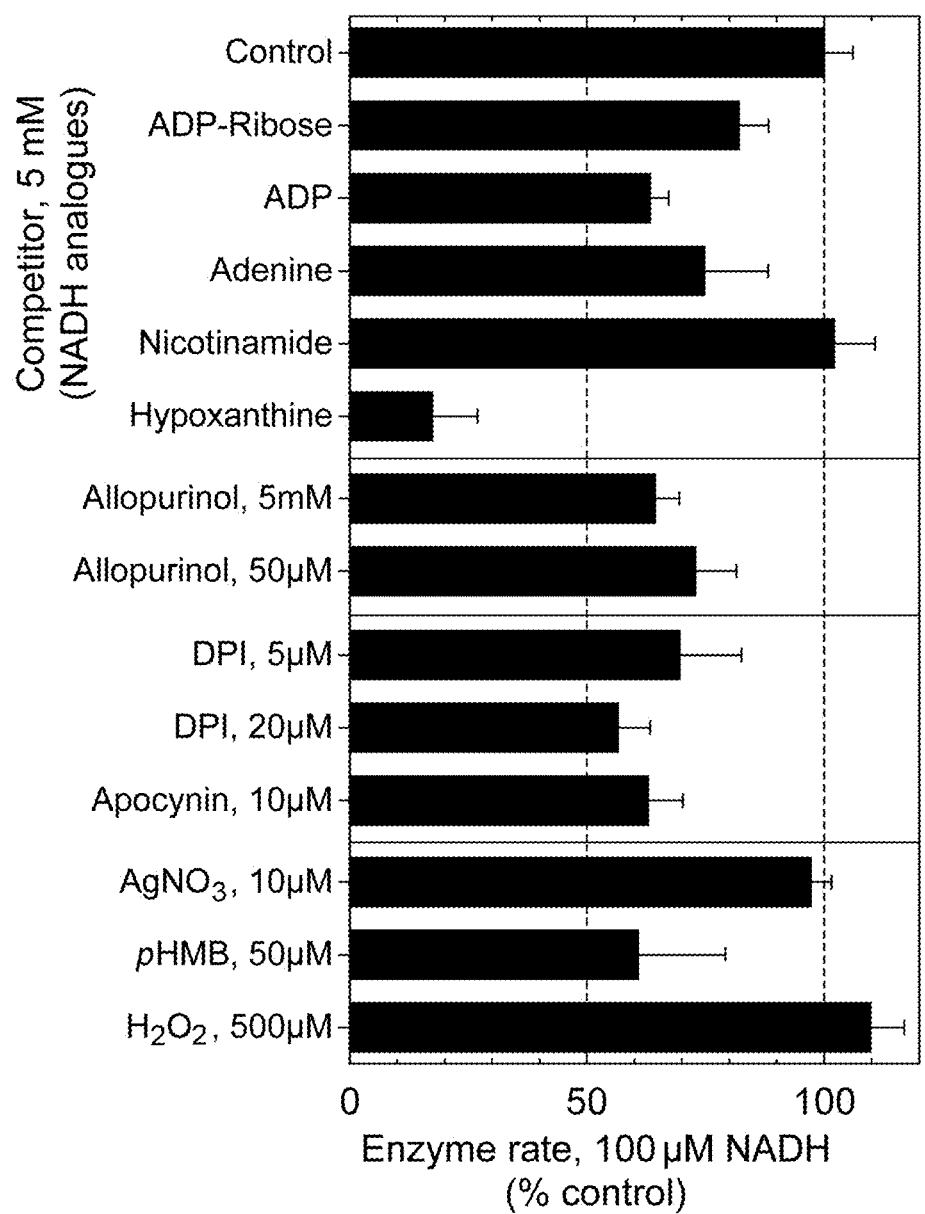
FIG. 9 is a graph demonstrating an inhibitor profile and pharmacology of *N. fowleri* Nfa-1 Hr (oxidase) in vitro. Enzyme activity in the presence of various substrate analogues and inhibitors were determined, including the NADH substrate analogue hypoxanthine ($K_i$=1 mM), the xanthine oxidase inhibitor Allopurinol ($K_i$=134 µM), the NAD(P)H oxidase inhibitors DPI (diphenyleneiodonium chloride) ($K_i$=19 μM) and Apocynin ($K_i$=17 μM), the NADH peroxidase inhibitors $AgNO_3$ ($K_i$=345 μM) and pHMB (para-hydroxymercuribenzoate) ($K_i$=78 μM), and the NADH peroxidase activator $H_2O_2$ (9.7% stimulation).

Enzyme activity in the presence of various substrate analogues and inhibitors were determined, including the NADH substrate analogue hypoxanthine ($K_i$=1 mM), the xanthine oxidase inhibitor Allopurinol ($K_i$=134 µM), the NAD(P)H oxidase inhibitors DPI (diphenyleneiodonium chloride) ($K_i$=19 µM) and Apocynin ($K_i$=17 µM), the NADH peroxidase inhibitors $AgNO_3$ ($K_i$=345 µM) and pHMB (para-hydroxymercuribenzoate) ($K_i$=78 µM), and the NADH peroxidase activator $H_2O_2$. The results are demonstrated in FIG. 9.

Example 6

Effect of Nfa-1 Inhibitors on *N. fowleri*-Induced Cytotoxicity

*Naegleria fowleri* strain Nf69 (ATCC 30215) was cultivated at about 33° C. in modified Nelson's medium (about 1 mM Na$_2$HPO$_4$, about 1 mM KH$_2$PO$_4$, about 2.05 mM NaCl, about 16.2 µM MgSO$_4$, about 27.2 µM CaCl$_2$, about 0.17 g/L DIFCO Liver infusion broth, about 9.4 mM glucose) supplemented with about 10% heat-inactivated fetal bovine serum. For cytotoxicity assays, Chinese hamster ovary (CHO) cells were grown at about 37° C. in DMEM medium supplemented with about 10% fetal bovine serum until cultures reached about 70-80% confluency. Subsequently cultures were infected with N. fowleri cells at a ratio of 1 N. fowleri amoeba per 5-10 CHO cells and co-cultivated overnight for about 13 hours at about 37° C. The cytotoxicity effect of N. fowleri amoebae on CHO cells was measured by an LDH-based cytotoxicity assay that quantifies the release of lactate dehydrogenase (LDH) from dead cells at 490 nm wavelength absorbance for calculation of amoeba-induced cytotoxicity to the mammalian host cells.

Figure 10:
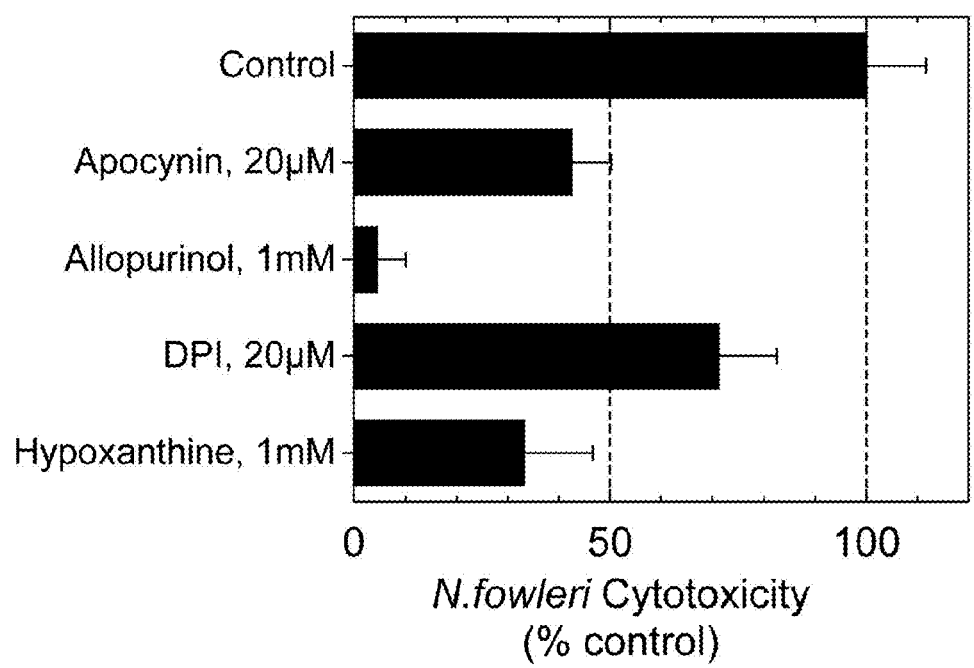
FIG. 10 is a graph demonstrating the effect of various compounds on the cytotoxicity of N. fowleri in vitro. Cytotoxicity of N. fowleri amoebae was measured with CHO cells co-cultured with N. fowleri for 13 hours at 37° C. using the LDH cytotoxicity assay (infection ratio of 1 amoeba cell per 5 CHO cells). Strong protection from the high levels of N. fowleri cytotoxicity in vivo was found for the oxidase inhibitors Apocynin ($IC_{50}$=15 μM), Allopurinol ($IC_{50}$=48 μM), DPI ($IC_{50}$=49 μM), and hypoxanthine ($IC_{50}$=497 μM).

Cytotoxicity of Naegleria fowleri amoebae was measured with CHO cells co-cultured with N. fowleri for about 13 hours at about 37° C. using the LDH cytotoxicity assay (infection ratio of 1 amoeba cell per 5-10 CHO cells) as described above. The results are demonstrated in FIG. 10. Protection from high levels of N. fowleri cytotoxicity in vivo was observed for Apocynin (IC$_{50}$=15 µM), Allopurinol (IC$_{50}$=48 µM), DPI (IC$_{50}$=49 µM), and hypoxanthine (IC$_{50}$=497 µM).

Example 7

ROS and Hydrogen Peroxide Production in N. fowleri

Figure 11A:
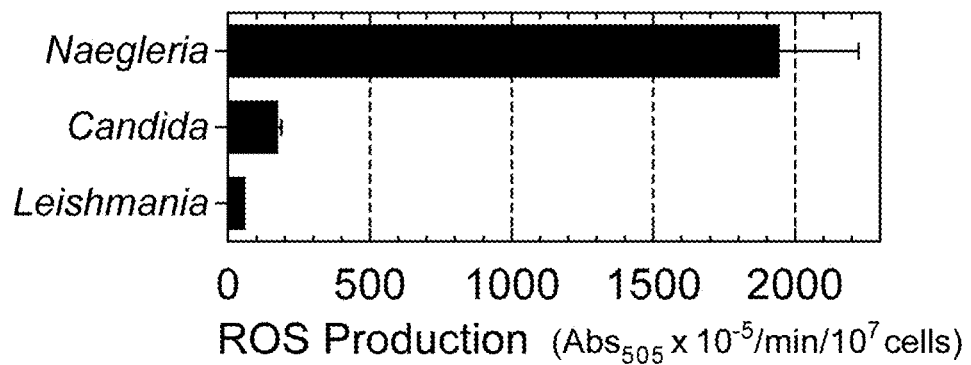
FIGS. 11A-11B show graphs demonstrating the production of reactive oxygen species (ROS) (FIG. 11A) or hydrogen peroxide (FIG. 11B).
Figure 11B:
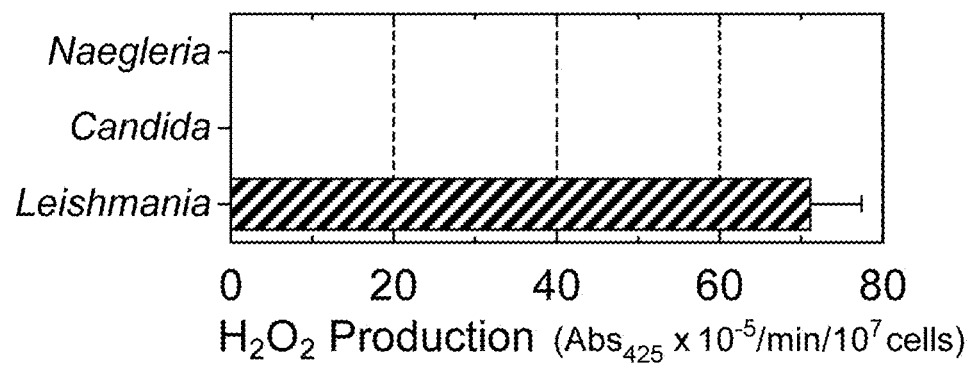

Production of reactive oxygen species (ROS) or hydrogen peroxide (H$_2$O$_2$) by in vitro cultures of N. fowleri amoebae was measured by Lucigenin assay (50 µM) at 505 nm absorbance for ROS production or by Luminol assay (1 mM) at 425 nm absorbance for H$_2$O$_2$ production, respectively. Candida albicans and Leishmania mexicana cultures were used as controls. Results are demonstrated in FIGS. 11A and 11B.

High levels of ROS production characteristic for xanthine oxidase-like enzymes were detected in live N. fowleri amoebae using the pathogenic fungus Candida albicans and the protozoan parasite Leishmania mexicana for comparison (Lucigenin assay at 50 µM, Abs 505 nm). In contrast, no significant levels of H$_2$O$_2$ production were detected in live N. fowleri amoebae or C. albicans (Luminol assay at 1 mM, Abs 425 nm).

We claim:

1. A method of reducing the pathogenicity of *Naegleria fowleri* in a subject in need thereof, the method comprising administering a therapeutically effective amount of apocynin to the subject in need thereof.

2. The method of claim 1, wherein the therapeutically effective amount of apocynin reduces cytotoxicity in the subject in need thereof.

3. The method of claim 1, wherein the therapeutically effective amount of apocynin reduces the amount of reactive oxygen species in the subject in need thereof.

4. The method of claim 1, wherein the therapeutically effective amount of apocynin reduces the oxidoreductase activity of a Nfa-1 protein in *Naegleria fowleri*.

* * * * *